United States Patent [19]

Warren, Jr.

[11] Patent Number: 4,478,577

[45] Date of Patent: Oct. 23, 1984

[54] ORTHODONTIC APPLIANCE

[76] Inventor: Richard F. Warren, Jr., 596 Granville Rd., Granville, Ohio 43023

[21] Appl. No.: 521,721

[22] Filed: Aug. 9, 1983

[51] Int. Cl.$^3$ .............................................. A61C 7/00
[52] U.S. Cl. .......................................... 433/14; 433/18
[58] Field of Search ................................. 433/14, 18

[56] References Cited

U.S. PATENT DOCUMENTS

| | | | |
|---|---|---|---|
| 3,235,965 | 2/1966 | Muir | 433/14 |
| 3,262,207 | 7/1966 | Kesling | 433/14 |
| 3,307,261 | 3/1967 | Steiner | 433/14 |
| 3,408,739 | 11/1968 | Johnson | 433/14 |
| 3,414,976 | 12/1968 | Steiner | 433/14 |
| 3,574,940 | 4/1971 | Allesee | 433/14 |
| 3,599,331 | 8/1971 | Lee | 433/14 |
| 3,606,685 | 9/1971 | Schwartz | 433/14 |
| 3,793,730 | 2/1974 | Begg et al. | 433/14 |
| 4,014,096 | 3/1977 | Dellinger | 433/14 |
| 4,037,324 | 7/1977 | Andreasen | 433/14 |
| 4,310,306 | 1/1982 | Wallshein | 433/14 |
| 4,322,206 | 3/1982 | Reynolds | 433/14 |

Primary Examiner—Robert Peshock
Attorney, Agent, or Firm—Millard & Cox

[57] ABSTRACT

An orthodontic appliance for counteracting rotational forces acting on a tooth where such forces originate from the action of an arch wire on the surface mounted conventional orthodontic bracket, said arch wire forces being primarily intended for the linear translation of the tooth. Rotational forces are counteracted by means of a lever arm that is rigidly attached to the conventional orthodontic bracket and in contact with the arch wire at a point spaced apart from the junction of the arch wire and the orthodontic bracket. The counteracting forces generated by the lever arm are proportional only to the rotational forces induced in the tooth by the force from the arch wire. The lever arm may also be configured with a shank capable of being inserted in a rectangular hole located in the conventional orthodontic bracket. Such an appliance is capable of being positively locked into the aforementioned rectangular hole by means of a deformable tail section.

6 Claims, 6 Drawing Figures

ORTHODONTIC APPLIANCE

FIELD OF THE INVENTION

The invention relates to an orthodontic appliance attachment for use in counteracting orthodontist applied forces which tend to rotate a tooth when such rotation is not desired. Additionally, the invention is related to an orthodontic appliance attachment for receiving and securely retaining an orthodontic elastic, wire or other such tooth-tooth or jaw-jaw device.

BACKGROUND OF THE INVENTION

The science and practice of orthodontia involve the reorienting or moving of teeth from one position to another not only to improve aesthetic appearance but also to improve the functioning of the teeth for their purposes of chewing food and maintaining a healthy mouth area. It is conventional to move the teeth by metallic bands around the teeth in combination with an arch wire and elastomeric members for applying various forces to the bands. The bands, elastomers and wire are interconnected by brackets rigidly mounted on the periphery of the bands.

Teeth are not rigidly held in the jaw bone but are capable of rotational and linear movement without damage to either the teeth or the jaw and without causing the teeth to be unduly loosened. This semi-fluid nature of the jawbone and the way teeth are attached thereto are the physical characteristics controlling the practice of orthodontia.

Some recent techniques involve the cementing of a bracket directly to the surface of the tooth. Thereafter, an arch wire, usually of a square or rectangular cross-section, is utilized in the conventional manner. It is lock-wired to the brackets by means of a thin ligature wire. When it is desired to move a tooth in a linear direction along the jaw, rubber bands or the like are adjusted to produce a force in the desired direction. The arch wire may be used for raising, lowering or rotating the tooth. The tooth being in a semi-free floating condition then begins to move in response to the forces applied. Problems arise because the force of linear translation is of necessity applied at the surface of the tooth thereby producing not only a linearly translating force but also a moment around the center of rotation of the tooth. Numerous methods have been utilized to avoid the undesirable rotation of a tooth as it is linearly translated including (1) anticipatory pre-rotation of a tooth in the opposite direction in order to have it arrive at its ultimate destination at a correct orientation and (2) post arrival corrective rotation.

In current aperture bounded on three sides by the bracket and on the fourth by the tooth to which it is attached. Said aperture may extend the full vertical length of the bracket in substantially the same direction as the tooth, that is, running from the root toward the crown. The aperture is of significance in two aspects of the invention described herein, one aspect being the tooth rotation problem described above and the second aspect being a means for attaching additional orthodontic bracketry to a tooth on which the apertured bracket is mounted.

Various additonal orthodontic bracketry may be mounted on the aperture bracket by means of pin like projections extending into said aperture; U.S. Pat. No. 4,310,306 to Wallshein is illustrative.

It is conventional to lock-wire the additional bracketry to the tooth brackets by using additional ligature wire to prevent inadvertent dislodgement during the orthodontic procedure or as the patient goes through his normal daily regiment.

SUMMARY OF THE INVENTION

Therefore, an orthodontic appliance has been developed for counteracting the rotational forces on a tooth that are caused by the force applied to said tooth by means of the arch wire. This appliance utilizes a substantially rigid lever arm that is fixedly attached to a tooth mounted orthodontic bracket, the lever then extending into contact with the arch wire at a point spaced apart from the junction of the arch wire and bracket. The lever arm then acts against the arch wire to oppose any rotational forces on the tooth that are caused by the force applied by the arch wire to the tooth via the tooth mounted bracket.

The lever arm is attached to the bracket by means of a transversely extending pin on one end which projects through the polygonal aperture of the bracket. To prevent relative rotation between the pin and the bracket, the pin is of the same polygonal cross-section as the aperture. Said pin is provided with a tail section which extends beyond the end of the aperture and may be deformed to lock the pin-shaped bracket within the aperture rather than relying on the friction forces of a ligature wire.

In another aspect of the invention involving a different orthodontic appliance, a pin-shaped element for use directly within the aperture is provided with a ball-shaped tip on one end and a deformable tail section on the other. The ball-shaped tip is suitable for receiving and retaining orthodontic elastics, ligature wires and other tooth-tooth or jaw-jaw devices.

DETAILED DESCRIPTION OF THE INVENTION

Figure 1:
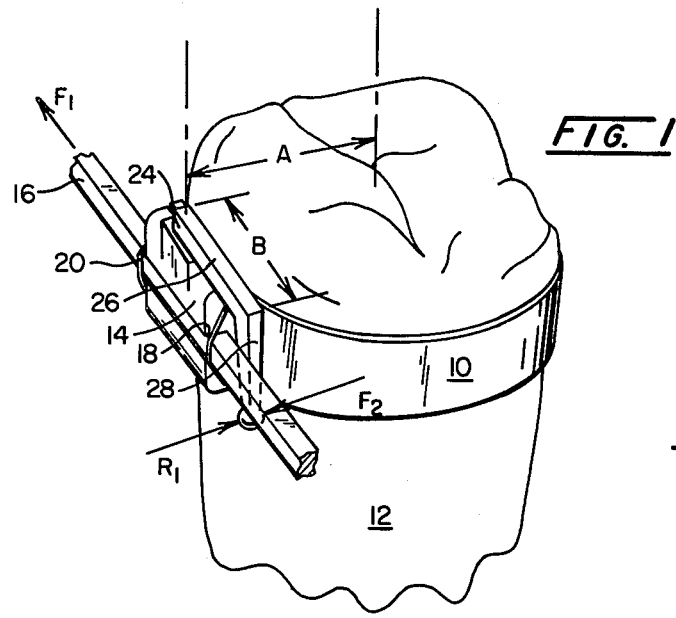
FIG. 1 is a perspective view of orthodontic apparatus on a typical tooth including one embodiment of the orthodontic apparatus showing a lever arm mounted on a tooth bracket according to the present invention.
Figure 2:
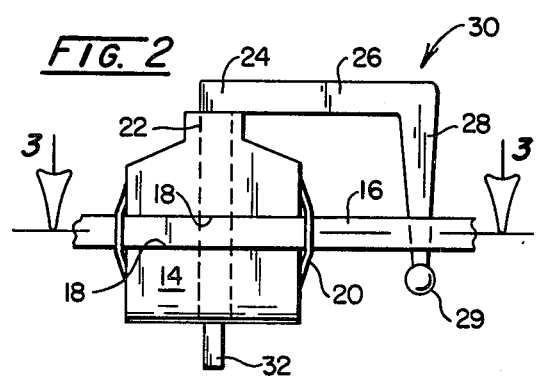
FIG. 2 is a side elevational view of the orthodontic bracket of FIG. 1.
Figure 3:
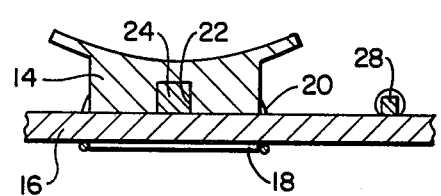
FIG. 3 is a sectional view taken along line 3—3 of FIG. 2.

Looking generally to FIGS. 1, 2 and 3, an orthodontic band 10 circumscribes tooth 12 and mounted on its periphery is a bracket 14. Some orthodontic practice allows the conventional orthodontic bracket 14 to be attached directly to the surface of tooth 12 rather than being attached to the band 10. For purposes of this invention, the mounting means is immaterial. Bracket 14 is configured to receive an arch wire 16 of rectangular cross-section in a horizontally extending slot 18, said arch wire being held in place upon bracket 14 by means of a ligature wire 20.

Mounted within a square or rectangular, longitudinally extending aperture 22 in bracket 14 is a shank 24 which supports a lever arm or horizontal section 26 at its upper end. A projection 28 depends from the distal end of lever arm 26 to lock behind arch wire 16. Projection 28, lever arm 26 and shank 24 together form a generally inverted U-shaped device 30. The purpose of shank 24 is to fixedly attach the U-shaped device 30 to bracket 14 and because of its rectangular or square cross-section which conforms to the longitudinal shape of aperture 22, to prevent rotation of the entire U-shaped device 30 within the aperture. Shank 24 terminates in tail 32 which is deformable to pervent the extraction of the device 30 from aperture 22 which effectively locks the bracket 14 between the deformed tail 32 and the lever arm 26.

It will be observed that projection 28 is of sufficient length that when U-shaped device 30 is locked within the aperture 22 and an arch wire 16 is located within slot 18, the projection will be in contact with the arch wire. The distance between the bracket 14 and the point of contact of projection 28 with the arch wire is the distance B. The greater the distance B, the less force that must be exerted upon the arch wire by the projection to balance the rotational force exerted on the bracket 14 by the tensioned arch wire 16. However, the distance B is typically no greater than is necessary to reach the space between the target tooth 12 and the adjacent tooth. Typically, the point of contact of projection 28 with arch wire 16 will be on the side of the wire on which the tooth is located, thereby minimizing the space taken up in the mouth by alien structure. It should be observed that projection 28 terminates in a ball-shaped tip 29 which is primarily designed to prevent puncture type wounds to the mouth and to prevent items from becoming impaled thereon. However, it serves an additional function. Note that the surface of projection 28 converges toward ball 29 and a groove is formed where they merge. It is intended that when the shank 24 slips into place in aperture 22, the arch wire 16 will simultaneously cam into place in the groove. Thereby the arch wire will serve as a detent-like lock to inhibit inadvertant transverse movement of device 30.

Also shown in FIG. 1 is a distance A. Distance A is the distance between the point of application of force by the arch wire 16 to the tooth 12 and the center of rotation of that tooth. In reality the distance A will vary from tooth to tooth and from patient to patient, however, there is a center of rotation of each tooth and it is generally not located at the surface of the tooth. The distance A is presented to emphasize the fact that the application of a force at the surface of a tooth produces not only linear movement in a tooth but also induces a rotational movement. Force $F_1$ is indicated as being applied by the arch wire 16 in the given direction; force F is adjusted by the orthodontist to produce the translation of the target tooth relative to the jaw. Additionally shown is a force $F_2$ which is shown being applied at the point of contact between lever arm projection 28 and arch wire 16. Also shown is reaction force $R_1$ which is the force applied to the projection 28 by to the arch wire 16. By applying the basic laws of physics the following relationships are known to be true:

$$F_1 \times A = F_2 \times B \qquad (1)$$

$$F_2 = R_1 \qquad (2)$$

These relationships are true in a static system. The present system is actually a dynamic system, but the rate of movement is so slow and occurs over such a long period of time that the system can be considered to be a nearly balanced static system. Not shown, of course, is the reaction force of the gums and jawbone to the linearly translating components of force $F_1$. Since force $F_2$ is equal to the reaction force $R_1$, there would be no rotational forces around the center of rotation of the tooth. The sum of the moments around the center of rotation of the tooth are as follows:

$$F_1 \times A + R_1 \times B = 0 \qquad (3)$$

Therefore, there is no rotation during orthodontic procedures employing a lever arm device such as the U-shaped device 30.

What remains is that the entire energy input of $F_1$ is directly toward linearly translating the tooth 12 rather than having a portion of that force being devoted to attempting to rotate the tooth. The result is that the tooth arrives at the desired location after linear translation with an orientation similar to the original orientation of the tooth. It is important to note that if no rotational forces are developed due to the resistance of the gums or the jawbone or other intervening forces, then in fact the reaction $R_1$ will be zero. It also will be appreciated that the reaction forces developed rely on the assumption that the U-shaped device 30 is substantially rigid.

The preferred embodiment illustrated in FIG. 1 includes a rectilinear-type lever arm comprising a horizontal section and two vertical sections. It is clear that the device 30 could be configured in other ways including a diagonal extension with its proximal end reaching from the top of the aperture 22 and its distal end extending to the point of application of the force some distance away from the bracket. It is also apparent that other forces may be resisted by this same technique including the tendency of a tooth to rotate about a horizontal axis of rotation due to the fact that the band or point of application of the force $F_1$ to the mounting bracket 14 occurs above the point at which the tooth is substantially anchored to the jawbone at the base of the tooth. This last problem is less prevalent in orthodontic practice since the location of a given target tooth is usually between two other teeth which will apply the counterrotating forces necessary to overcome any tendency to rotate about a horizontal axis of rotation. However the end tooth at the end of a row of teeth, as for example the last molar, may have these problems. It will also be appreciated that the lever arm assembly will properly function in the absence of the pin 24 if the proximal end of horizontal section 26 or its diagonal equivalent is fixedly attached to the orthodontic bracket 14 as by soldering or welding.

Turning now to FIGS. 2 and 3, the orthodontic bracket 14 has received a four-sided rectilinearly-shaped shank 24 and the tail 32 is shown below the bracket. The tail 32 may be deformed such that its free end is misaligned with the aperture 22 to thereby securely lock the pin in place without the use of ligature wires. The shank 24 is fixedly attached to the proximal end of horizontal section 26 which is of sufficient length B based upon the strength of the material from which it is made to produce the reaction forces to prevent rotation of a tooth. In this configuration the projection 28 which depends from the distal end of horizontal section 26 is shown contacting the arch wire 16 on the same side of the arch wire as the tooth would lie. Therefore, any force exerted by the U-shaped element would be toward the viewer in FIG. 2. A ball-shaped tip 29 depends from projection 28 to prevent injury to the wearer.

When the U-shaped device 30 is mounted in an orthodontic bracket and brought into contact with the arch wire there is no force being applied. The only forces that will be exerted by the lever arm against the arch wire are those developed in reaction to the attempted rotation by the tooth to which the orthodontic bracket is attached. Those forces only develop after the tooth has attempted to translate in a linear direction and the force applied to the tooth to promote that linear translation is also producing a moment about the center of rotation of the tooth. Until such a moment about the center of rotation of the tooth develops there is no reaction force. Thus, at all times as shown in Equation (3) above the sum of the moments about the center of rotation of the tooth will always remain zero.

Figure 4:
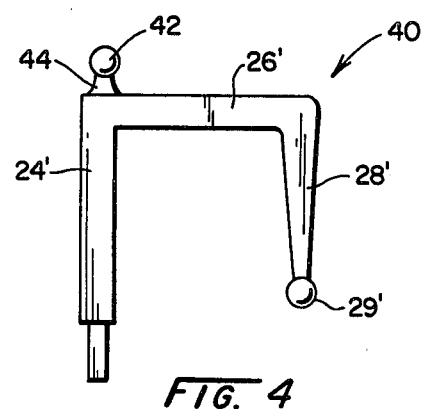
FIG. 4 is an alternative embodiment of the lever arm according to the present invention.

Looking now at FIG. 4 which is an alternative embodiment 40 of the U-shaped device 30. The only distinction being a ball 42 formed on the proximal end of lever arm 26' immediately above shank 24'. Its function will be explained subsequently in relation to FIGS. 5 and 6. The shank or vertical section 24' is connected to the horizontal section 26' which is of appropriate length to transmit the forces in a substantially rigid way from the point of application of the force by the arch wire to the vertical section 28', the length of the horizontal section 26' being based upon the material being utilized, its thickness and the forces to be overcome. Again, this configuration terminates in a ball-shaped tip 29' at the end of the vertical section 28'. The embodiment shown in FIG. 4 has a second ball-shaped tip 42 located immediately above the shank 30' which is also useful for receiving an orthodontic elastic or other jaw-jaw and tooth-tooth orthodontic restraining device. The ball tip 42 sits atop a neck section 44. The neck section 44 serves the combined purposes of raising the ball tip 42 sufficiently above the surface of the lever arm structure 40 and away from the orthodontic bracket in which it is installed thereby facilitating the insertion and removal of orthodontic elastics or other such devices. The neck section 44 has a smaller cross-sectional area than does ball tip 42. This change in cross-sectional area between the ball tip and the neck portion prevents any elastic or wire which is wrapped around the neck section from inadvertently slipping over the ball tip which is retaining said elastic or wire in place on the lever arm structure 40. In order for an elastic or wire to slip from the neck and over the ball tip that is retaining it in the neck region, the elastic must expand or deform. Since this is unlikely except in the intervention of an outside force, the elastic or wire will be appropriately retained on the ball tip and neck assembly between patient appointments thereby assuring that the orthodontic procedures being performed on that patient are properly carried forward.

Figure 5:
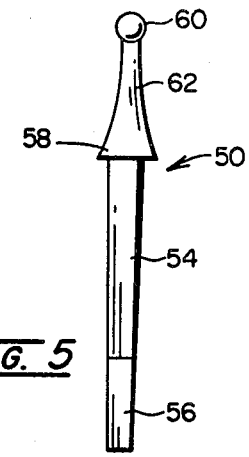
FIG. 5 is a front elevational view of a locking pin type device with ball-shaped tip according to the present invention.
Figure 6:
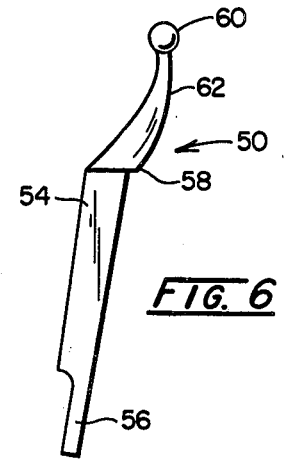
FIG. 6 is a side-elevational view of the locking pin of FIG. 5.

Turning now to FIGS. 5 and 6, a pin-type appliance 50 is illustrated and designed for insertion into the above-described rectangular aperture 22. The shank 54 of the pin is configured to be retained within the aperture 22 in such a way that it will not rotate within said aperture. The shank may be configured to gently taper toward it tail end 56 so that the act of inserting the pin within said aperture is facilitated since greater clearances to the internal dimensions of said aperture are provided at the lower portion of the pin at which insertion is begun. Those clearances diminish to a fairly tight fit as the shank is fully inserted. The deformable tail section 56 is of sufficient length that it can be grasped with an appropriate tool (as for example pliers) and deformed in an outward direction to lock the pin within the aperture as described previously in relation to the tail 32 on U-shaped device 30. Only a minor amount of deformation is required in order to appropriately lock pin within the aperture. Of course, the tail section 56 should not be so long as to cause discomfort to the patient once it has been deformed.

Residing atop the shank section 54 of the appliance is a shoulder 58 which is larger than both the dimensions of the slot and the uppermost part of the shank section. Therefore, the shoulder 58 will come to rest on the shelf surrounding the opening of aperture 22, thereby providing a mechanical stop against which the pin comes to rest after it has been inserted. Between the action of the shoulder 58 and the deformed tail 56, the pin is securely locked within the aperture. It will be observed in FIG. 2 that lever arm 26 serves as the shoulder means device 30 and separately formed shoulder means are not necessary where a lever arm is attached.

Above the shoulder 58, and away from the shank 54 is a ball 60 which resides on a tapered neck section 62. The tapered neck section 62 extends between the shoulder 58 and the ball 60 and is configured to offset the ball from the axis of the shank 54. The offset facilitates the insertion and removal of orthodontic elastics which are to be installed over the ball. The cross-sectional area of the neck 62 immediately adjacent to the ball 60 is smaller than the cross-sectional area of the ball. The significance of this change in cross-sectional area has been previously described. The offset provided by neck 62 is in such a direction that the ball is offset away from the gum area of the target tooth upon which the orthodontic bracket and appliance are mounted. An additional purpose for the offsetting of the ball away from the center line of the shank 54 is to prevent the orthodontic elastic or ligature wire installed over such a ball from interfering with other orthodontic apparatus installed on the target or adjacent teeth or with the function and meshing of the teeth in a patient's mouth.

It will be appreciated that numerous changes and modifications may be made in the above-described embodiments of the invention without departing from the scope thereof. Accordingly, the foregoing description is to be construed in an illustrative and not in a limitative sense, the scope of the invention being defined solely by the appended claims.

I claim:

1. In the combination of a bracket mounted on a tooth, an arch wire and means for inhibiting rotation of both said tooth and said bracket with respect to said arch wire, the bracket including a slot in its surface which faces away from said tooth, said slot being linearly extending in a direction generally perpendicular to the length of the tooth which extends from its root to its crown, two sides of the slot being planer and parallel, a linearly extending aperture in said bracket of polygonal shape extending the full length thereof in a direction perpendicular to said slot, said aperture being in the surface of said bracket which faces toward said tooth, the arch wire (1) including two planer surfaces parallel to each other, (2) being disposed within said slot and extending therefrom, and (3) planer surfaces being juxtaposed to the planer sides of the slot, said arch wire being confined in the slot by ligature wire, a rigid device U-shaped mounted with one leg of the device within the aperture, the leg in the aperture being of a mating polygonal shape to the aperture such that relative rotation of the two is prevented, the other leg of the U-shaped device being juxtaposed to the arch wire and spaced from the bracket, said other leg projecting from one planer surface of the arch wire toward the other and on the side of the arch wire nearest the tooth and terminating in a rounded shape, means forming a groove between said rounded shape and the rest of the other leg, said arch wire being wedged into said groove, a ball mounted on said U-shaped device adjacent said shoulder by a neck section which is reduced in diameter as compared to said ball.

2. The combination of claim 1 including a shoulder on the polygonally shaped leg for engaging the bracket to stop penetration of the leg at the desired depth.

3. The combination of claim 2 including a deformable tail on the end of the polygonally shaped leg remote from said shoulder, said tail being deformed to lock its associated leg in place.

4. The combination of claim 3 wherein the leg in the aperture tapers from a larger to a smaller size toward its end having the tail.

5. The combination of claim 1 wherein the leg in the aperture tapers from a larger to a smaller size toward its end having the tail.

6. In the combination of a bracket mounted on a tooth, an arch wire and a pin for mounting on said bracket, said pin serving to anchor orthodontic elastics, the bracket including a slot in its surface which faces away from said tooth, said slot being linearly extending in a direction generally perpendicular to the length of the tooth which extends from its root to its crown, two sides of the slot being planer and parallel, a linearly extending aperture in said bracket of polygonal shape extending the full length thereof in a direction perpendicular to said slot, said aperture being in the surface of said bracket which faces said tooth, the arch wire (1) including two planer surfaces parallel to each other, (2) being disposed within said slot and extending therefrom, and (3) planer surfaces being juxtaposed to the planer sides of the slot, said arch wire being attached to the bracket by ligature wire, the pin being mounted within the aperture, said pin being of a mating polygonal shape to prevent relative rotation of the pin and bracket, the end of the pin nearest the crown of the tooth being formed to prevent pin withdrawl, a shoulder on the other end of said pin abutting said bracket to prevent the pin from being drawn through the aperture to a greater extent than desired, a tapered neck section projecting from the end of the pin nearest the root of the tooth, the neck section tapering from a larger to a smaller cross section away from the shoulder, said neck section terminating in an enlarged ball, the point of merger of the neck section and the ball being of reduced cross-sectional area to define a groove for retaining orthodontic elastics, the neck section curving outwardly from the root of the tooth to accommodate the gum and minimize gum to elastic contact.

\* \* \* \* \*